US00PP23698P3

(12) United States Plant Patent
Zwetzig

(10) Patent No.: US PP23,698 P3
(45) Date of Patent: Jul. 2, 2013

(54) ***HIBISCUS* PLANT NAMED 'NEW OLD YELLA'**

(50) Latin Name: *Hibiscus moscheutos×H. coccineus*
Varietal Denomination: New Old Yella

(75) Inventor: Gretchen Zwetzig, Lindsay, CA (US)

(73) Assignee: Gretchen Zwetzig, Lindsay, CA (US)

( * ) Notice: Subject to any disclaimer, the term of this patent is extended or adjusted under 35 U.S.C. 154(b) by 130 days.

(21) Appl. No.: 12/932,389

(22) Filed: Feb. 24, 2011

(65) Prior Publication Data

US 2012/0222181 P1 Aug. 30, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — June Hwu

(57) ABSTRACT

A New and distinct cultivar of winter hardy *Hibiscus* plant named 'New Old Yella' is the result of a unique hybridization. This new and distinct cultivar is characterized primarily as to its novelty by its extreme cold hardi ness to Zone 4, its large thick-textured, light yellow flowers and its "Maple-shaped" leaves with a green coloration, Compactness of about 3 feet, its vigorous and uniform growth habit and its floriferous nature from midsummer until frost.

1 Drawing Sheet

Latin name: *Hibiscus moscheutos×H. coccineus.*
Varietal denomination: 'New Old Yella', hardy *Hibiscus.*

FIELD OF THE INVENTION

This plant, as a hybridized hardy *Hibiscus*, is valuable to the landscape market for its improvements in thicker textured and luminescent yellow colored flowers and buds, refined "maple-like" foliage with a soft green color, its all-around vigor, compact breaking action, and adaptation to extreme environments, including the ability to consistently survive winter temperatures of at least −30 degrees Fahrenheit.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Small refined, 3-5 lobed 'maple-shaped' leaves with a green color and relatively smooth margins which combined compliments the landscape;
(b) Medium-sized flowers that are outstanding for their luminescent yellow colored, thick textured petals;
(c) The plant being very floriferous with flowers that stay open for at least one full day, sometimes up to 2 days;
(d) The plant being small to medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'New Old Yella' was the result of a 50-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 2001 and was selected by Gretchen Zwetzig on her property located at 8101 S. 14th St. Lincoln, Nebr. 68516. Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown at 2½ years in the attached photographs.

More specifically, FIG. 1 is a close-up of the flower and the leaf.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart (2001), while general color recitations are consistent with ordinary American terminology.

'New Old Yella' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4) and Lindsay, Calif. (USDA Zone 9).

THE PLANT

Parentage:

*Seed parent.—Hibiscus moscheutos,* unnamed and unpatented Fleming-bred seedling.

*Pollen parent.—Hibiscus coccineus,* unnamed and unpatented Fleming-bred seedling.

Comparison between observed plant and parents: Observed Plant is 2½ foot shorter than parents and has a darker yellow flower.

Comparison between observed plant and other known cultivars: Observed Plant is unique, but most similar to 'Old Yella' U.S. Plant Pat. No. 13,630 and the other patented Fleming hardy *Hibiscus* in that:

(a) They are all compact at approximately 3 feet on average. But, 'New Old Yella' is apx. 1 foot shorter than 'Old Yella'.

(b) They are hardy to −30 degrees Fahrenheit.

(c) They all have refined new leaf shapes and colors.

(d) They all have thick, new flowers with new colors that bloom from the top to the bottom of the plant. 'New Old Yella' has flowers that are slightly more yellow than 'Old Yella'.

Origin: A selected seedling from stated cross.

Type of plant: Hardy, herbaceous perennial.

Classification: Variety of hardy *Hibiscus* plant.

Propagation: Relatively easy to propagate by cuttings in approximately 2 weeks; holds its distinguishing characteristics through successive cuttings and divisions.

Size: About 2½-3 feet tall and about 2 feet wide.

Form: Symmetrical annual growth from perennial roots.

Habit: Upright and uniformly branched.

Growth: Vigorous; medium and compact. Full grown (2½-3 ft) in 2 years.

Hardiness: Hardy to at least −30 degrees Fahrenheit.

General health: Plant is very disease resistant against rot, aphids, spider mites, scale, white fly etc.; sturdy through excessive drought, rain or wind.

Foliage:

1. *Arrangement.*—Alternate.
2. *Shape.*—Juvenile: 3-5 lobed "maple-shaped" leaves. Rounded base shape. Mature: Refined, "maple-shaped", 3-5 lobed leaf with entire to mildly serrate margins and acute apices; rounded base.
3. *Size.*—Mature leaf (petiole base to apex): Length is about 4 inches or (10 cm), width is about 5 inches or (12.5 cm).
4. *Color.*—Young leaves (upper side): 137-A and 137-B. Mature leaves: (upper side): 147 A. Veins: 61-A. Venation pattern: Palmate. Upper side mature leaf. Coloration of the mature lower leaf surface: Closest to; a little lighter than 146 B.
5. *Surface texture.*—Low sheen. Upper: Smooth. Lower: Semi-smooth.
6. *Petiole length.*—About 2¾ inches or 5.94 cm. Petiole diameter: 2 cm.
7. *Petiole color.*—146 B. Petiole surface texture: Semi-smooth.

Stems: The stems are stout at the base, becoming more slender toward the apices; coloration is consistent with the petiole. Length: 2-3 inches on average. Diameter: 2 cm. Internode length: 2 inches on average. Stem texture: Semi-smooth. Stem color: 147 B.

Blooming period: Profuse from June/July until frost, depending on South/North U.S.

Flower diameter: Medium; about 8-9 inches (20.32-22.86 cm).

Borne: Singly in the leaf axils, from midpoint of stems upward.

Bloom duration: Individual bloom lasts at least one full day; possibly up to 2 days.

Form: Campanulate; petals are also very overlapping.

Average number of flowers per season: Approximately 300.

Bud:

1. *Length.*—About 1¾ inches or (4.5 cm) on day before opening. Diameter: 1-2 inches.
2. *Color.*—2-C.
3. *Surface texture.*—Semi-glabrous.
4. *Duration.*—One to two weeks.

Corolla: Having five petals.

1. *Petal character and dimensions.*—Campanulate and very overlapping. (a) Length: About 3¾ inches or (9.5 cm). (b) Width: About 4½ inches or (11.5 cm).
2. *Coloration.*—Light yellow. (a) Light yellow petals: 2-D and 11-D. Coloration of lower petal surface: 11-D. (b) Upper and lower Venation in petals: A little darker than 11-D. (c) Eye zone: 45-B. Size: 1½ inches or (3.8 cm).
3. *Texture.*—Smooth.
4. *Substance.*—Thick.
5. *Shape.*—Campanulate and very overlapping.

Reproductive organs:

1. *Staminal column.*—Stamen along basal two-thirds. One per flower. Filaments: Apx. 100 stamens per flower. Staminal length: About 1½ inches or (3.8 cm). Stamen color Designation: 2-D. Pollen color: 12-B.
2. *Style.*—Terminates upper one-third of staminal column. Length ½ to 1 inch. Color: 11 A. Stigmatic lobe color: 11-A.

Calyx: Shape: 5 lobed, connate at the base; about 2½ inches or (6.35 cm) in length. One per flower. Upper and lower surface Color: Between 146-A and 146-B. Surface texture: Semi-smooth.

Stipules: None.

Epicalyx: Whorl of bracts.

1. *Shape.*—10-12 slender, sword-shaped bractlets.
2. *Length.*—About 1¼ inches or (3.175 cm).
3. *Upper and lower surface color.*—143-A.

Peduncle:

1. *Length.*—About 1½ inches or (3.81 cm).
2. *Strength.*—Stiff and sturdy. Surface texture: Semi-smooth.
3. *Color.*—Light to medium green with slight reddish-purple cast. 146-A with 61-C.

Seeds (fruit): Size: 1 cm. Color: Grey-brown. Average number: Less than 100.

The invention claimed:

1. A new and distinct cultivar of hardy *Hibiscus* plant, as herein shown and described, characterized by its compact nature, refined "maple-like" foliage of a green coloration, its large glowing light yellow flowers, its vigor and its hardiness.

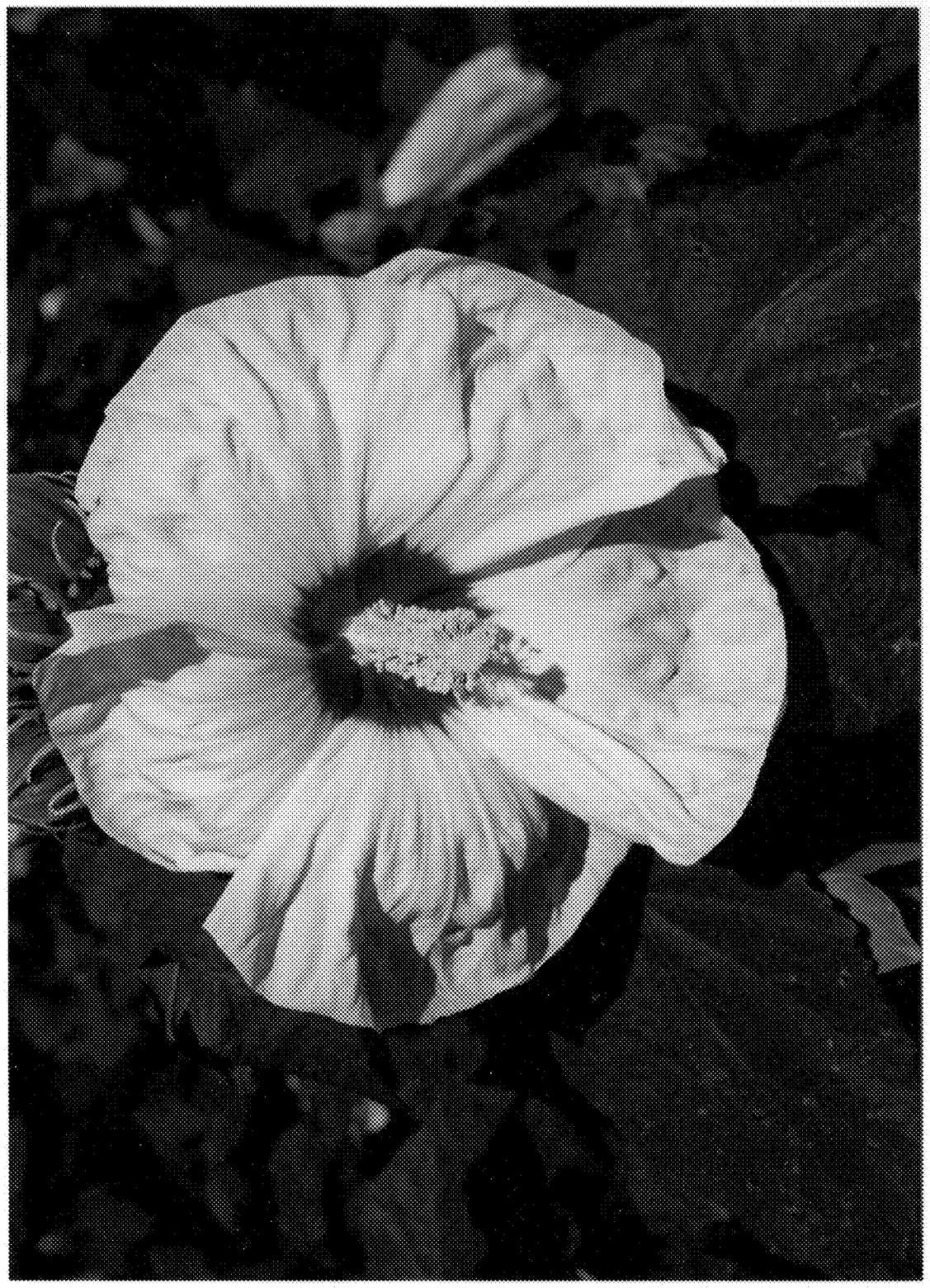

* * * * *